(12) United States Patent
Reisfeld (10) Patent No.: US 6,633,773 B1
(45) Date of Patent: Oct. 14, 2003

(54) AREA OF INTEREST RECONSTRUCTION FOR SURFACE OF AN ORGAN USING LOCATION DATA

(75) Inventor: Daniel Reisfeld, Haifa (IL)

(73) Assignee: Biosene, Inc., New Brunswick, NJ (US)

( * ) Notice: Subject to any disclaimer, the term of this patent is extended or adjusted under 35 U.S.C. 154(b) by 356 days.

(21) Appl. No.: 09/675,783

(22) Filed: Sep. 29, 2000

(51) Int. Cl.[7] ................................................. A61B 5/05
(52) U.S. Cl. ........................ 600/407; 600/481; 382/128
(58) Field of Search ................................ 600/407, 410, 600/481, 508; 382/128, 130, 131, 132

(56) References Cited

U.S. PATENT DOCUMENTS

| | | | |
|---|---|---|---|
| 3,316,896 A | 5/1967 | Thomasset | |
| 4,157,572 A | 6/1979 | Kennedy et al. | 360/33 |
| 4,459,990 A | 7/1984 | Barnea | 128/656 |
| 4,522,212 A | 6/1985 | Gelinas et al. | 128/642 |

(List continued on next page.)

(List continued on next page.)

FOREIGN PATENT DOCUMENTS

| | | |
|---|---|---|
| EP | 0 501 993 | 6/1997 |
| EP | 0 974 936 | 1/2000 |
| WO | WO 94/04938 | 3/1994 |
| WO | WO 94/06349 A1 | 3/1994 |
| WO | WO 96/05768 | 2/1996 |
| WO | WO 97/24983 | 6/1997 |
| WO | WO 97/24981 A2 | 7/1997 |
| WO | WO 97/24981 A3 | 7/1997 |
| WO | WO 97/25101 | 7/1997 |
| WO | WO 98/12663 | 3/1998 |
| WO | WO 98/35720 A3 | 8/1998 |
| WO | WO 98/35720 A2 | 8/1998 |
| WO | WO 99/05971 | 2/1999 |
| WO | WO 00/07501 | 2/2000 |

OTHER PUBLICATIONS

Gerstenfeld E., Sahakian A., Swiryn S.; Evidence for Transient Linking of Atrial Excitation During Atrial Fibrillation in Humans (1992); Circulation vol. 86, No. 2, pp 375–382.
Gerstenfeld E., Sahakian A., Baerman J., Ropella K., Swiryn S.; Detection of Changes in Atrial Endocardial Activation With Use of an Orthogonal Catheter (1991); JACC vol. 18, No. 4, pp 1034–1042.

(List continued on next page.)

*Primary Examiner*—Philip H. Leung
(74) *Attorney, Agent, or Firm*—Louis J. Capezzuto; Frederick L. Herman (57) ABSTRACT

A method is provided for generating a three-dimensional reconstruction of a portion of a surface of an organ, and, in particular, a portion of the surface of a chamber of the heart. The reconstruction is generated from location data of a plurality of acquisition points on the organ surface. The method comprises computing a two-dimensional reference plane based on the location data. A function that describes the surface is computed, wherein each point on the surface may be described as a function of the reference plane. The function is then bounded to a constrained region. Tessellation of the function facilitates computer display of the reconstruction. If the location data is accompanied by physiologic property data characteristic of the tissue, the method may be used to generate a reconstruction of the tissue property as a function of the tissue geometry.

39 Claims, 6 Drawing Sheets

U.S. PATENT DOCUMENTS

| | | | | |
|---|---|---|---|---|
| 4,628,937 A | | 12/1986 | Hess et al. ................ | 128/642 |
| 4,630,203 A | * | 12/1986 | Szirtes ...................... | 382/132 |
| 4,660,571 A | | 4/1987 | Hess et al. ................ | 128/784 |
| 4,682,603 A | | 7/1987 | Franz ........................ | 128/642 |
| 4,699,147 A | | 10/1987 | Chilson et al. ............ | 128/642 |
| 4,762,124 A | | 8/1988 | Kerch et al. .............. | 128/156 |
| 4,875,165 A | | 10/1989 | Fencil et al. ........... | 364/413.22 |
| 4,878,115 A | | 10/1989 | Elion ........................ | 358/111 |
| 4,898,181 A | | 2/1990 | Kessier ..................... | 128/699 |
| 4,905,705 A | | 3/1990 | Kizakevich et al. ....... | 128/696 |
| 4,911,174 A | | 3/1990 | Pederson et al. .......... | 128/695 |
| 4,922,912 A | | 5/1990 | Watanabe .................. | 128/642 |
| 4,940,064 A | | 7/1990 | Desai ........................ | 128/784 |
| 4,955,382 A | | 9/1990 | Franz et al. ............... | 128/642 |
| 4,962,767 A | | 10/1990 | Brownlee .................. | 128/786 |
| 4,979,510 A | | 12/1990 | Franz et al. ............... | 128/642 |
| 5,022,396 A | | 6/1991 | Watanabe .................. | 128/642 |
| 5,038,791 A | | 8/1991 | Collins et al. ............. | 128/696 |
| 5,042,486 A | | 8/1991 | Pfeiler et al. .............. | 128/653 |
| 5,056,524 A | | 10/1991 | Oe ............................. | 128/654 |
| 5,127,403 A | | 7/1992 | Brownlee ............... | 128/419 P |
| 5,156,151 A | | 10/1992 | Imran ........................ | 128/642 |
| 5,175,773 A | * | 12/1992 | Garreau et al. ............ | 382/130 |
| 5,215,103 A | | 6/1993 | Desai ........................ | 128/784 |
| 5,227,969 A | | 7/1993 | Waggener et al. ..... | 364/413.26 |
| 5,228,442 A | | 7/1993 | Imran ........................ | 128/642 |
| 5,231,995 A | | 8/1993 | Desai ........................ | 128/784 |
| 5,239,999 A | | 8/1993 | Imran ........................ | 128/642 |
| 5,243,981 A | | 9/1993 | Hudrlik ..................... | 607/11 |
| 5,255,678 A | | 10/1993 | Deslauriers et al. ....... | 128/642 |
| 5,255,679 A | | 10/1993 | Imran ........................ | 128/642 |
| 5,279,299 A | | 1/1994 | Imran ........................ | 128/642 |
| 5,293,869 A | | 3/1994 | Edwards et al. ........... | 128/642 |
| 5,297,549 A | | 3/1994 | Beatty et al. .............. | 128/642 |
| 5,311,866 A | | 5/1994 | Kagan et al. .............. | 128/642 |
| 5,313,943 A | | 5/1994 | Houser et al. ............. | 128/642 |
| 5,324,284 A | | 6/1994 | Imran ........................ | 606/15 |
| 5,341,807 A | | 8/1994 | Nardella .................... | 128/642 |
| 5,345,936 A | | 9/1994 | Pomeranz et al. ......... | 138/642 |
| 5,383,917 A | | 1/1995 | Desai et al. ............... | 607/702 |
| 5,391,199 A | | 2/1995 | Ben-Haim ................. | 607/122 |
| 5,409,000 A | | 4/1995 | Imran ........................ | 128/642 |
| 5,433,198 A | | 7/1995 | Desai ........................ | 128/642 |
| 5,443,489 A | | 8/1995 | Ben-Haim ................. | 607/115 |
| 5,454,370 A | | 10/1995 | Avitall ....................... | 128/642 |
| 5,471,982 A | | 12/1995 | Edwards et al. ........... | 128/642 |
| 5,485,849 A | | 1/1996 | Panescu et al. ............ | 128/699 |
| 5,487,391 A | | 1/1996 | Panescu ..................... | 128/699 |
| 5,515,853 A | | 5/1996 | Smith et al. ........... | 128/661.01 |
| 5,531,227 A | | 7/1996 | Schneider ............... | 128/653.1 |
| 5,546,951 A | | 8/1996 | Ben-Haim ................. | 128/702 |
| 5,549,109 A | | 8/1996 | Samson et al. ............ | 128/642 |
| 5,588,432 A | | 12/1996 | Crowley ............... | 128/660.03 |
| 5,595,183 A | | 1/1997 | Swanson et al. ........... | 128/697 |
| 5,637,090 A | | 6/1997 | McGee et al. ............. | 604/95 |
| 5,657,755 A | | 8/1997 | Desai ........................ | 128/642 |
| 5,697,377 A | | 12/1997 | Wittkampf ................ | 128/696 |
| 5,718,241 A | | 2/1998 | Ben-Haim et al. ......... | 128/702 |
| 5,730,704 A | | 3/1998 | Avitall ....................... | 600/374 |
| 5,738,096 A | | 4/1998 | Ben-Haim ............... | 128/653.1 |
| 5,755,664 A | | 5/1998 | Rubenstein ................ | 600/377 |
| 5,840,031 A | | 11/1998 | Crowley .................... | 600/440 |
| 5,842,984 A | | 12/1998 | Avitall ....................... | 600/374 |
| 5,871,019 A | * | 2/1999 | Belohlavek ................ | 600/450 |
| 5,889,524 A | * | 3/1999 | Sheehan et al. ........... | 345/419 |
| 5,921,924 A | | 7/1999 | Avitall ....................... | 600/374 |
| 5,931,835 A | | 8/1999 | Mackey ..................... | 606/34 |
| 5,931,863 A | | 8/1999 | Griffin, III et al. ......... | 607/122 |
| 5,999,587 A | * | 12/1999 | Ning et al. ................. | 378/4 |
| 6,052,618 A | | 4/2000 | Dahlke et al. ............. | 600/523 |
| 6,066,094 A | | 5/2000 | Ben-Haim ................. | 600/437 |

OTHER PUBLICATIONS

Kadish A., Spear J., Levine J., Hanich R., Prood. C., Moore E.; Vector Mapping of Myocardial Activation (1986); Laboratory Investigation Arrhythmia vol. 74, No. 3, pp 603–615.

Kass et al.; Proceedings of First International Conference Vision (1987); Snakes: Active Contour Models; pp 259–268.

Terzopoulos D.; Transactions on Pattern Analysis and Machine Intelligence (1986), vol. PAMI–8, No. 4; Regularization of Inverse Visual Problems Involving Discontinuities; pp 413–424.

Lai et al.; IEEE Transactions on Pattern Analysis and Machine Intelligence (1995) vol. 17, No. 11; Deformable Contours: Modeling and Extraction; pp 1084–1090.

Onnasch et al.; Computers in Cardiology, Long Beach, CA IEEE Computer Society (1975); A Versatile Program for the Documentation and Comparison of Traced Heart Contours; pp 257–262.

Duda et al.; Communications of the ACM (1972) vol. 15, No. 1; Use of the Hough Transformation to Detect Lines and Curves in Pictures; pp 11–15.

Castelman, K.R.; Digital Image Processing (1996); "Curve and Surface Fitting"; pp. 501–507.

Jain, A.K.; Fundamentals of Digital Image Processing (1989); "The Back–Projection Operator"; pp. 439–445.

Foley J.D., van Dam A., Feiner S.K., Hughes J.F.; 2nd Edition in C Computer Graphics Principles and Practice (1996);"Filling Algorithms"; pp. 979–986.

Besl, Paul J., Member, IEEE, and McKay, Neil D.; IEEE Transactions on Pattern Analysis and Machine Intelligence, vol. 14. No. 2, Feb. 1992; A Method for Registration of 3–D Shapes; pp. 239–256.

Lai, Kok Fung; Thesis, University of Wisconsin–Madison 1994; Deformable Contours: Modeling, Extraction, Detection and Classification; 96 pgs.

Umeyama, Shinji; IEEE Transactions on Pattern Analysis and Machine Intelligence, vol. 13, No. 4, Apr. 1991; Least–Squares Estimation of Transformation Parameters Between Two Point Patterns; pp. 376–380.

Freeman, H.; "Computer Processing of Line Drawing Images"; Computing Surveys 6, 1974, pp. 57–97.

Fang, Shu–Cherng; Puthenpura, Sarat; AT&T; Linear Optimization and Extensions; Theory and Algorithms; Complexity Analysis and the Ellipsoid Method, Chap. 5, pp 96–103.

* cited by examiner

AREA OF INTEREST RECONSTRUCTION FOR SURFACE OF AN ORGAN USING LOCATION DATA

FIELD OF THE INVENTION

The present invention is directed to methods and apparatus for reconstructing a portion of a surface of an organ from location data of a plurality of points on the organ surface. The invention is particularly directed at three-dimensional reconstruction of a portion of a surface of a heart chamber.

BACKGROUND OF THE INVENTION

A number of techniques have been proposed for reconstructing the surface of a body organ based on location data of sample points on or near the organ surface. One such technique is disclosed in U.S. patent application Ser. No. 09/122,137 and in its corresponding European Patent Application 974,936 filed on Jul. 23, 1999. In a preferred embodiment of the '137 application, an initial, closed 3D curve, preferably, an ellipsoid, is defined in the volume of the sampled points. The initial closed curve either encompasses most of the sample points or is interior to substantially all of the points. A grid of desired density is defined on the curve and the curve is adjusted by adjusting the grid points to resemble the configuration of the organ surface. The technique of the '137 application works well for reconstructing a chamber of a heart where ample location data has been collected at representative points on the chamber surface.

The method of the '137 has been proposed for reconstructing a map of the heart chamber which, in addition to depicting chamber geometry, also shows a physiological property of the tissue in the chamber. Illustrative physiological properties include electrical properties such as local activation time or peak voltage, or mechanical properties such as tissue contractility. The resultant maps may be used for directing therapy to specific tissue that harbors a particular pathology.

Cardiologists are increasingly looking to shorten the duration of cardiac procedures, including electrophysiology procedures. Also, cardiologists have access to other modalities that allow them to diagnose pathology and localize it to a particular region or area of interest in the heart. Thus, in many cases, it is no longer necessary to reconstruct a map of the entire cardiac chamber based on data sampled throughout the chamber. Rather, it is desirable to provide diagnostic methods which permit the reconstruction of only a portion of a surface of an organ. Unfortunately, the method of the '137 application does not always accurately reconstruct the surface of a portion of the organ absent representative data taken throughout the organ. Thus, there exists a need for methods and apparatus which allow for accurate reconstruction of areas of interest within an organ without reconstructing the organ as a whole.

SUMMARY OF THE INVENTION

One aspect of the present invention is directed to a method of generating a three-dimensional reconstruction of a portion of a surface of an organ. The reconstruction is generated from location data of a plurality of acquisition points on the organ surface. Each of the acquisition points has a three-dimensional location on the organ surface. The method comprises computing a two-dimensional reference plane based on the location data. A function that describes the surface is then computed, wherein each point on the surface may be described as a function of the reference plane. The function is then bounded to a constrained region.

The reference plane generated by the method of the invention exhibits errors with respect to the three-dimensional locations of the acquisition points. In some embodiments, the plane is computed by minimizing the errors from the acquisition points to the plane.

In some embodiments, the plane is computed by minimizing the mean square error between the acquisition points and the plane.

In some embodiments, in minimizing the errors from the plane to the acquisition points, the errors are weighted. In one weighting scheme, higher weights are accorded to isolated location data points.

In some embodiments, the plane calculated in the method of the invention passes through the center of a bounding ellipsoid surrounding the acquisition points. In other embodiments, the plane passes through the center of mass of a convex hull of the acquisition points. In still other embodiments, the plane passes through the center of mass of the acquisition points.

In some embodiments, the function calculated in the method of the invention passes through the acquisition points. Exemplary functions are splines and radial basis functions. Alternatively, the function may be a piecewise linear function, formed, for example, by triangulation of the location data points.

In some embodiments, the value of the function corresponding to a point on the plane is a weighted average of the locations of the acquisition points. One way of weighting the acquisition points in calculating the value of the function is to weight the acquisition points by their respective distances from that point on the plane.

In some embodiments of the method of the invention, the function is bounded by a convex hull of the projection of the location data points onto the plane.

In some embodiments, the method of the invention may comprise tessellating the function. Where the function is tessellated, in some embodiments, vertices of the tessellation may be made to coincide with at least some of the location data points. Tessellation may be performed, for example, by Delaunay triangulation of the reference plane.

The method of the invention may further comprise refining the tessellation by adding virtual points to the surface. The value of the virtual points may be determined from the function.

Another embodiment of the method of the invention comprises computing a two-dimensional reference plane based on the location data. A function that describes the surface is then computed, wherein each point on the surface may be described as a function of the reference plane. The function is then tessellated.

In some embodiments, for example, when the tessellation is performed by Delaunay triangulation, the tessellation also serves to bound the function to a constrained region.

In some embodiments, the method of the invention further comprises displaying the reconstruction.

In some embodiments, the location data used in the method of the invention may be associated with data characteristic of a property of the tissue at the acquisition points. In that case, the method of the invention may further comprise displaying the reconstruction, wherein the reconstruction comprises geometrical information as well as tissue property information of the data acquisition points. The reconstruction may further comprise property information intermediate the acquisition points. The reconstruction may be colored so as to indicate the value of the property information.

In some embodiments, the method of the invention is directed to generating a reconstruction of a portion of the surface of a heart.

The location data used in the method of the invention may be acquired with a catheter comprising a position sensor. In some embodiments, the position sensor is an electromagnetic position sensor.

Another aspect of the invention is directed to apparatus for generating a three-dimensional reconstruction of a portion of a surface of an organ from location data of a plurality of acquisition points on the organ surface. Each of the acquisition points has a three-dimensional location on the organ surface. In one embodiment, the apparatus of the invention comprises a computer processor which computes a two-dimensional reference plane based on the location data. The processor then computes a function that describes the surface, wherein each point on the surface may be described as a function of the reference plane. The processor then bounds the function to a constrained region.

In another embodiment of the apparatus of the invention, the processor computes a two-dimensional reference plane based on the location data. The processor then computes a function that describes the surface, wherein each point on the surface may be described as a function of the reference plane. The processor than tessellates the function. In some embodiments, such as where tessellation is performed by Delaunay triangulation of the reference plane, the tessellation serves to bound the function to a constrained region.

In some embodiments of the invention, the instructions for the computer processor are embodied in computer software.

In some embodiments, the apparatus of the invention further comprises dedicated graphics circuitry which may perform some of the above-named tasks of the computer processor as well as additional calculations involved in displaying the reconstruction.

In some embodiments, the apparatus of the invention further comprises a display.

In some embodiments of the apparatus of the invention, location data of each of the acquisition points is associated with data characteristic of a property, such as an electrical property, of tissue at the points. In such a case, the apparatus of the invention may provide a reconstruction which represents both the geometry and the tissue property of the portion of the organ.

In some embodiments, the apparatus of the invention further comprises a catheter, the catheter comprising at least one electrode and at least one position sensor. In some embodiments, the at least one position sensor comprises an electromagnetic position sensor.

The features and advantages of the invention will be more readily apparent from the detailed description set forth below, taken in conjunction with the accompanying drawings.

DETAILED DESCRIPTION OF PREFERRED EMBODIMENTS

The present invention is directed to a method and apparatus for generating a three-dimensional reconstruction of a portion of a surface of an organ from location data of a plurality of acquisition points on the organ surface. The location data of the acquisition points comprises the three-dimensional locations of the points.

The organ being reconstructed according to the method and apparatus of the invention may be any organ in the body such as the heart, the kidneys or the liver. In particular, the method and apparatus of the invention are applicable to generating a three-dimensional reconstruction of a portion of a chamber of a heart.

The method and apparatus of the invention are equally amenable to generating a three-dimensional reconstruction of a portion of either the inner or outer surface of the target organ.

The location data used in the method of the invention permits the reconstruction of a map which depicts the three-dimensional geometry of a portion of the target organ. If the location data of each of the acquisition points is associated with property data characteristic of the tissue at those points, the method and apparatus of the invention may be used to reconstruct a map of the portion of the organ showing both geometry and one or more tissue properties. Illustrative properties that may be mapped according to the method and apparatus of the invention include chemical, mechanical and electrical properties of the tissue. For example, electrical properties of heart tissue may comprise the local activation time or the peak voltage at which the tissue is activated. A mechanical property may comprise, for example, the contractility of the heart tissue.

U.S. Pat. No. 5,546,951 and U.S. patent application Ser. No. 08/793,371 and its corresponding application filed under the Patent Cooperation Treaty and published as WO 96/05768, which are incorporated herein in their entirety by reference, disclose methods for sensing an electrical property of the heart tissue, for example, local activation time, as a function of the precise location within the heart. The data are acquired with one or more catheters that are advanced into the heart, the catheters having electrical and location sensors in their distal tips. Methods of creating a map of the electrical activity of the heart based on these data are disclosed in commonly assigned U.S. patent application Ser. No. 09/122,137 filed on Jul. 24, 1998 and in its corresponding published European Patent Application no. EP 974,936, as well as in U.S. patent application Ser. No. 09/357,559 filed on Jul. 22, 1999, the disclosures of which are also incorporated herein in their entirety by reference.

Catheters containing position sensors may be used to determine the trajectory of points on the cardiac surface.

These trajectories may be used to infer the motion characteristics such as the contractility of the tissue. As disclosed in U.S. Pat. Nos. 5,738,096 and 6,066,094, incorporated herein in their entirety by reference, maps depicting such motion characteristics may be constructed when the trajectory information is sampled at a sufficient number of points in the heart.

Figure 1:
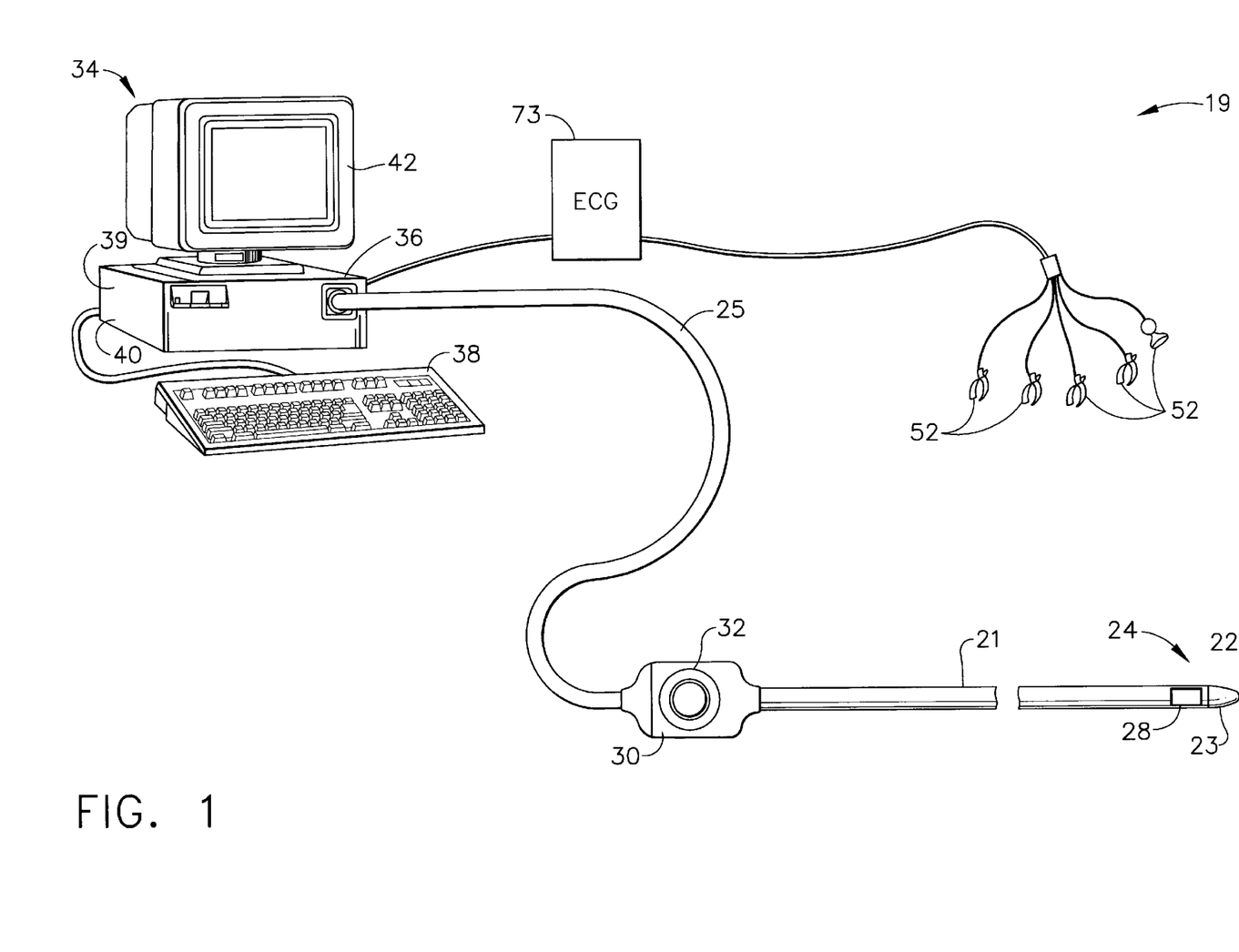
FIG. 1 shows elements of an exemplary catheter system useful for acquiring location and property data endocardially for use in the method of the invention.
Figure 2:
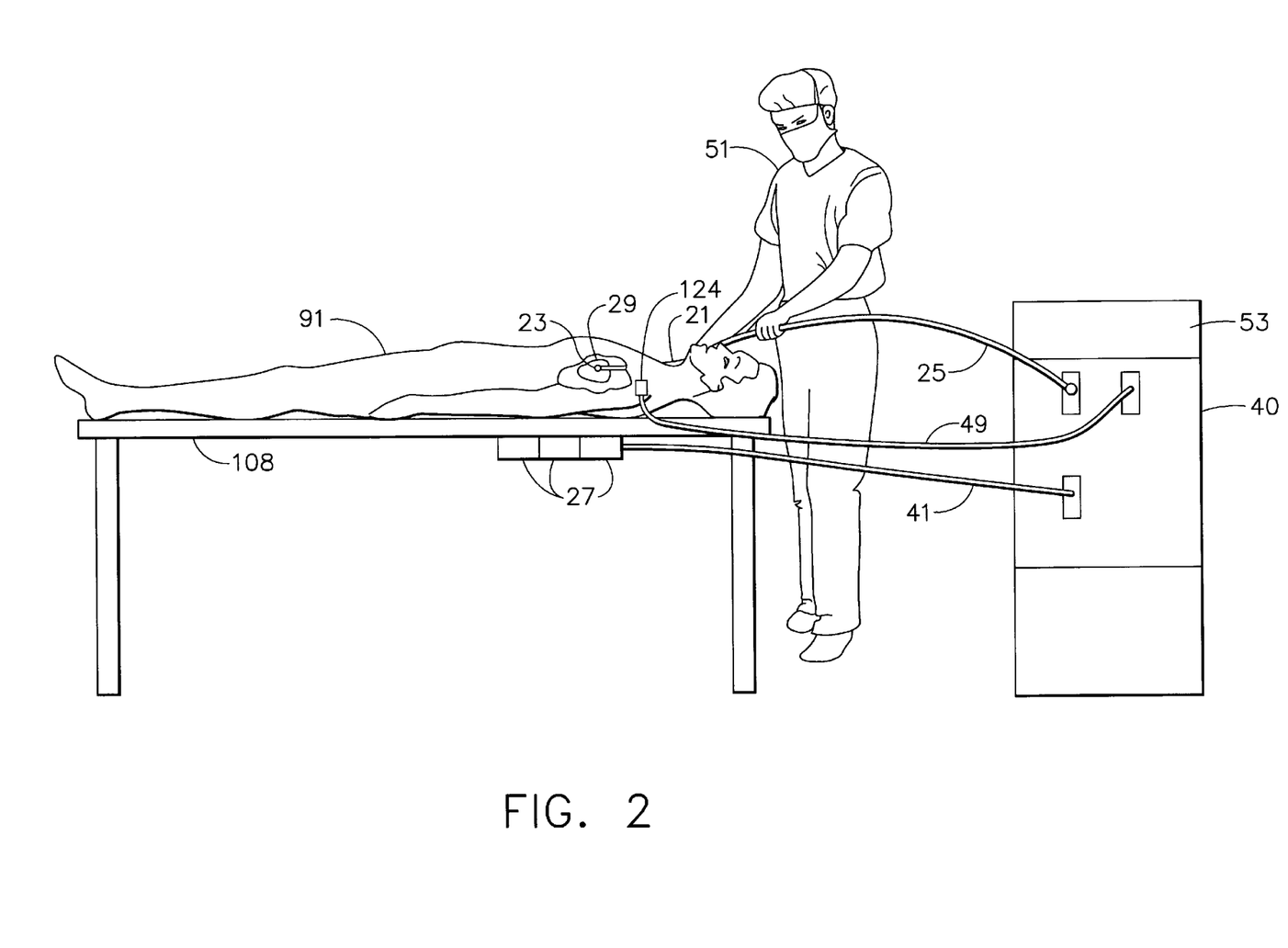
FIG. 2 shows additional elements of the catheter system of FIG. 1.

FIG. 1 and FIG. 2 show elements of an exemplary catheter system useful for acquiring location and property data endocardially for use in the method of the invention. For simplicity, the following description will refer to the method and apparatus as being applied to reconstructing a portion of the surface of a chamber of a heart, although it is the intention of the inventor not to limit the scope of the invention to this organ. The apparatus shown in FIG. 1 and FIG. 2 includes catheter 21 for intravascular insertion into the human body. Distal end 24 of catheter 21 includes electrode 23 adjacent to catheter distal tip 22 for recording intracardial electrical data, as described, for example, in U.S. Pat. No. 5,391,199 or in PCT application W097/24983, which are incorporated herein by reference. Alternatively or additionally, distal end 24 of catheter 21 may also include other diagnostic apparatus for recording parameter values at points within the body, and may also include therapeutic apparatus as is known in the art.

Catheter 21, used in the apparatus of the invention for acquiring electrical data for use in the method of the invention, may have more than one electrode 23 contained therein. Catheters containing multiple electrodes are described, for example in U.S. Pat. Nos. 5,409,000; 5,588,432; 5,931,863; 5,931,835; and 5,921,924, and in U.S. patent application Ser. No 09/506,766 which are hereby incorporated herein in their entirety by reference. The use of multi-electrode catheters in collecting intracardiac electrograms for use in the method and apparatus of the invention permit the simultaneous measurement of electrical data at multiple points in the heart chamber, which can potentially decrease the time required for collecting such data at a plurality of sites within the heart.

As shown in FIG. 2, local electrical and location data are acquired by advancing catheter 21 having electrode 23 at its distal tip 22 to an acquisition point in the heart, preferably contacting the tissue at that point with electrode 23 contained at the catheter distal tip 22, whereupon the electrical data, typically in the form of the electrical potential, is acquired over some time period. Typically, the local electrical data at each point are acquired as a function of time for a period of several cardiac cycles. The data are then stored in computer memory for future use, as described hereinbelow.

In the embodiment illustrated in FIG. 1, catheter distal end 22 includes a position sensor 28 that generates signals used to determine the location, and, in some embodiments, the orientation of the catheter within the body. Position sensor 28 is preferably adjacent to electrode 23 in a fixed relation with tip 22. In one embodiment, position sensor 28 comprises three coils, such as described in PCT application W096/05768, which is incorporated herein in its entirety by reference.

The position sensor 28 enables continuous generation of up to six dimensions of position and orientation information with respect to externally applied magnetic fields. Alternatively, position sensor 28 may comprise other position and/or coordinate sensors as described in U.S. Pat. No. 5,391,199, U.S. Pat. No. 5,443,489 and in PCT application W094/04938, which are incorporated herein by reference.

Measurements of the catheter distal tip 22 locations at the acquisition points on the cardiac surface are used in the computation of the geometry of that portion of the cardiac surface. Measurement of electrical data from electrode 23 together with catheter tip locations at the acquisition points permits the computation of a map of the property of the cardiac tissue as a function of the tissue geometry according to some embodiments of the present invention. By way of example, the NAVI-STAR™ catheter, available from Biosense-Webster, Inc. of Diamond Bar, Calif., is a catheter having both an electrode and a position sensor that may be useful in measuring location and electrical property data for use in practicing the present invention. Further, tip 22 may be coated with an opaque marking material to visualize the tip under an imaging apparatus such as a fluoroscope.

The three-dimensional coordinates of position sensor 28 are typically determined relative to the position of a reference sensor 124 (FIG. 2). The reference sensor 124 is also preferably an electromagnetic sensor that operates according to the same principles as the position sensor 28 in catheter 21. The reference sensor 124 may be positioned external to the patient, for example, as part of an adhesive patch applied to the patient's skin as shown in FIG. 2. Alternatively, the reference sensor 124 may be positioned internal to the patient, for example, as a component of a reference catheter that is positioned at a particular point in the heart of the patient during the acquisition of the location and electrical property measurements. Thus, the position sensor 28 in catheter 21 provides the three-dimensional coordinates of the catheter tip 22 relative to the reference position sensor 124.

In constructing a map of the property of a portion of the heart, the coordinates of the catheter tip 22 during acquisition of electrical data are typically referenced to a particular point in the cardiac cycle, for example, to the end diastole portion of the cardiac cycle, which may be determined, for example, from body-surface electrograms.

Catheter 21 preferably includes a handle 30, having controls 32 that are used to steer distal end 24 of catheter 21 in a desired direction. Catheter 21 preferably comprises a steering mechanism in distal end 24 as is known in the art to facilitate repositioning of tip 22.

Catheter 21 is coupled via an extension cable 25 to a console 34 which enables the user to observe and regulate the function of catheter 21. Console 34 preferably includes a computer 36, keyboard 38, signal-processing circuitry 40, which are typically inside computer 36, and display 42. Signal processing circuits 40 typically receive, amplify, filter and digitize signals from catheter 21, including signals from position sensor 28 and electrode 23, whereupon these digitized signals are used by computer 36 to process the electrograms and to compute the position and/or orientation of catheter tip 22. Alternatively, appropriate circuitry may be associated with catheter 21 itself so that circuits 40 receive signals that are already amplified, filtered and/or digitized. Computer 36 also contains a processor 39 for computing a reference plane based on the location data acquired via position sensor 28 of catheter 21. Processor 39 also calculates and bounds the function that describes the portion of the reconstructed cardiac surface. In some embodiments, processor 39 also tessellates the function. Preferably, computer 36 includes a memory for storing position and electrogram information. Processor 39 in computer 36 also functions, in some embodiments of the invention, to compute a map of the property of the cardiac tissue. In some embodiments, computer 36 further comprises dedicated graphics circuitry for displaying the map of the heart property. The computer 36 shown in FIG. 1 is also equipped to receive body surface ECG signals from ECG monitor 73 that is connected to a plurality of ECG body surface leads 52. Alternatively, ECG monitoring may also be conducted directly by signal processing circuits 40.

As shown in FIG. 2, a physician 51 inserts catheter 21 through an incision in the vasculature, e.g., using an intravascular approach, into a chamber of a heart 29 of a patient 91, so that electrode 23 of catheter distal tip 22 and position sensor 28 are inside the heart chamber. In accordance with an exemplary position sensor described in PCT patent application number WO 96/05768, filed Jan. 24, 1995, and in U.S. Pat. No. 5,391,199, which are assigned to the assignee of the present application and whose disclosures are incorporated herein in their entirety by reference, sensor 28 generates signals in response to externally applied magnetic fields generated by electromagnetic field generator coils 27 fixed to operating table 108 in proximity to patient 91. The magnitude of the signals generated by sensor 28 depends on the position and orientation of the sensor in the applied magnetic field. Field generator coils 27 are connected via cable 41 to driver circuits which are part of signal processing circuits 40. Circuits 40 control the operation of the generator coils 27 and the overall position sensor location system.

Alternatively, the catheter system for obtaining local electrograms for use in the present invention may employ field generator coils in the catheter and sensors external to the patient.

While the catheter system has been described herein with reference to electromagnetic position sensors, any other sensor that provides three-dimensional position information and, optionally, orientation information, may be used in obtaining the location data for practice of the method of the present invention. Illustrative sensors that are also useful include acoustic sensors and magnetic sensors. For example, acoustic sensors of the type disclosed in U.S. Pat. No. 5,409,000 and in PCT application WO 99/05971, the disclosures of which are incorporated herein in their entirety by reference, may be used in the catheter system to obtain the electrograms for use in the method of the invention.

As disclosed in U.S. Pat. No. 5,391,199, mapping a property, particularly an electrical property of the heart, is performed by positioning the distal tip 22 of catheter 21 at a site (acquisition point) within the heart, sensing location and electrical information at the site, processing the sensed location and electrical information at the site to create a data point, and repeating these steps a sufficient number of times to create a map of the property of the heart. For an accurate map of the property based on chamber electrical activity, location and electrical data are preferably sensed when electrode 23 at distal tip 22 of catheter 21 is in contact with or in close proximity to the cardiac wall at each site.

Computation of Two-dimensional Reference Plane

The first step in the method of the invention is computing a two-dimensional reference plane based on the location data. This plane is computed as follows:

The reference plane may be found by modifying a statistical technique for reducing the dimension of a high dimensionality space called Principal Component Analysis. This technique is also known under the names Karhunen-Loève procedure, factor analysis and Hotelling transform.

Let X be an n-dimensional random vector. Then X can be represented without error by an expansion of the form $$X = \sum_{i=1}^{n} y_i \phi_i = \Phi Y$$

where $Y = [y_1 \ldots y_n]^T$ and $\Phi = [\phi_1 \ldots \phi_n]^T$ is an orthonormal matrix, whose columns form an orthonormal basis. Therefore: $y_i = \phi_i^T X$.

Suppose that we determine only m<n components of Y (determine a plane (m=2) from a three dimensional space, (n=3)), but we want to estimate X as best as possible. We use constants, $b_i$, instead of the components of Y we do not calculate:

$$\overline{X} = \sum_{i=1}^{m} y_i \phi_i + \sum_{i=m+1}^{n} b_i \phi_i$$

As applied to the method of the invention, we seek to determine a two-dimensional reference plane which approximates the three-dimensional locations of the acquisition points. The plane will exhibit errors with respect to the three-dimensional locations of the acquisition points. In computing the plane, we seek to minimize these errors. In some embodiments, we use the mean-square error as a criterion to measure the effectiveness of the subset of m vectors:

$$\varepsilon^2(m) = E(\|X - \overline{X}\|^2) = \sum_{i=m+1}^{n} E((y_i - b_i)^2)$$

wherein E( ) is the average value of the expression within the brackets ( ).

We would like to make a choice which minimizes the mean square error from the reference plane to the locations of the acquisition points:

$$\frac{\partial}{\partial b_i} \varepsilon^2(m) = -2(E(y_i) - b_i) = 0$$

The mean-square error may be written as:

$$\varepsilon^2(m) = \sum_{i=m+1}^{n} (y_i - E(y_i))^2 = \sum_{i=m+1}^{n} \phi_i^T(X - E(X))(X - E(X))^T \phi_i = \sum_{i=m+1}^{n} \phi_i^T \Sigma_x \phi_i$$

where $\Sigma_x$ is, by definition, the covariance matrix of X.

As shown in K. Fukunaga, Introduction to Statistical Pattern Recognition, Academic Press, 1972, the optimum choice for the $\phi$s is those which satisfy $$\Sigma_x \phi_i = \lambda_i \phi_i$$

that is, the eigenvectors, $\phi_i$ of $\Sigma_x$. Arranging the eigenvalues $\lambda_i$ in a decreasing order $$\lambda_1 > \lambda_2 > \ldots > \lambda_n > 0$$

The minimum mean-square error is $$\min \varepsilon^2(m) = \sum_{i=m+1}^{n} \lambda_i$$

This minimum is achieved over all choices of orthonormal basis vectors, that is, for all isometries.

In our case n=3, m=2 and the unknown vectors are the locations of the acquisition points, $X_i$. The reference plane we are computing is the plane which is spanned by the two eigenvectors which correspond to the two highest eigenvalues, i.e., the first two principal components of the orthonormal basis.

The above calculation of the reference plane ensures that the reference plane passes through the center of mass of the acquisition points. However, the locations of the acquisition points are not generally evenly spaced. We may therefore, apply one or two of the following modifications to the above-mentioned technique. First, instead of looking for optimal rotation around the average, E(X), of the distribution, we may use the center of the bounding ellipsoid of the location data. In other words, instead of finding the eigenvalues and eigenvectors of $\Sigma_x$, we look for the eigenvalues and eigenvectors of M, wherein M is defined as $$M = (X-O)(X-O)^T$$

where O is the center of the bounding ellipsoid or the convex hull of the location data, since this center is not sensitive to the distribution of the points.

The bounding ellipsoid may be found by the following technique: Let $X_i = (x_i, y_i, z_i)$ be the ith location data point. Using homogeneous coordinates $\overline{X}_i = (x_i, y_i, z_i, 1)$, the affine transformation $T(\overline{X}) = A\overline{X}$ such that A is an affine matrix and $\|A\overline{X}_i\| \leq 1$ transfers the location data points to the unit sphere, i.e., the transformation determined by the matrix $A^{-1}$ transfers the unit sphere to an ellipsoid.

We are looking for the minimal bounding ellipsoid. This is determined by the transformation that result in the minimal volume, i.e., the determinant of A should be minimal. This is a linear optimization problem and any linear optimization technique (such as the simplex or ellipsoid method as described, for example in Linear Optimization and Extensions: Theory and Algorithms, S-C Fang and S. Puthenpura, Prentice Hall, Englewood Cliffs, N.J., pp. 96–103) will find the minimal bounding ellipsoid.

A second modification to the above-described technique is the association of a density weight, $1 \geq \delta_i > 0$, with each acquisition point $X_i$, such that the location of each acquisition point $X_i$ may be replaced in the covariance matrix or in the expression $$M = (X-O)(X-O)^T$$

by $\delta_i X_i$. The weights $\delta_i$ may be determined according to the following equation:

$$\delta_i = \frac{1}{\sum_j (\|X_i - X_j\|^2 + 1)^{-1}}$$

The value of $\delta_i$ is approximately equal to 1 when $X_i$ is an isolated point far removed from other points; $\delta_i \approx 1/n$ when all the n points are taken at the same location; intermediate values are obtained according to the density of the samples. Applying this type of weight to the acquisition point locations accords a higher weight to isolated points than to proximate points. Weighting each entry in the autocorrelation matrix, $\Sigma_x$, or in the matrix M in this manner further reduces the dependency of the calculation of the reference plane on the density of the sample points.

Calculation of Function That Describes the Surface

Having found the reference plane as described above, we now wish to find the function which describes the surface. The function will, ideally pass through the acquisition points and will also approximate the surface between these points.

We are looking for $f: R^2 \rightarrow R^1$ such that $f(x_i, y_i) \approx z_i$ for each acquisition point $P_i = (x_i, y_i, z_i)$ where the coordinates are given in the frame of reference of the principal components described above. In other words, we seek to find the function f from the plane to the acquisition points which defines a z value for the surface for each x, y position on the plane. The function f may be defined by a variety of techniques such as by using splines or radial basis functions.

In one embodiment of the invention, we define the function of a point on the reference plane as a weighted average of the locations of the acquisition points, and, more precisely, as a weighted average of the distance of each of the acquisition point locations from the point on the reference plane. The weights for the acquisition point locations may be defined according to the following scheme:

Let (x,y) be a point on the reference plane. We use the following weights:

$$w_i(x, y) = \frac{1}{((x-x_i)^2 + (y-y_i)^2)^k + c}$$

where c>0 is small (for example, $10^{-6}$). Preferably, the constant k has a value of about 1. The function that approximates the surface (the approximation function) is then given by the expression:

$$f(x, y) = \frac{\sum w_i(x, y) z_i}{\sum w_i(x, y)}$$

When $c \rightarrow 0$, $f(x,y)$ interpolates the sample points, i.e., $f(x_i, y_i) = z_i$. As the value of c increases, the resultant function is smoother and a less accurate approximation of the acquisition point locations.

Bounding and Tessellating the Function

The previous two stages result in an analytical function that describes the surface. We now need to constrain the function to the area of interest, i.e., to the neighborhood of the acquisition points.

In one embodiment of the invention, Delaunay triangulation is used to bound the function. In addition, Delaunay triangulation also has the effect of tessellating or discretizing the function, which offers the added benefit of enabling the rendering of the surface by modern computer graphics techniques or enabling other computations involving the surface. As disclosed by M. de Berg et al. in Computational Geometry Algorithms and Applications, Springer, 1991, Delaunay triangulation is a method that results in an optimal triangulation of the convex hull of the points.

Let $P = \{p_1, p_2, \ldots, p_n\}$ be a set of points in the plane. We define a triangulation as a subdivision s such that no edge connecting two vertices can be added to s without intersecting one of the existing edges, wherein an edge is a straight line segment connecting any two points. Any edge $e = \overline{p_i p_j}$ connecting two consecutive points $p_i$ and $p_j$ on the boundary of the convex hull of P is an edge in any triangulation. Otherwise, it is incident to two contiguous triangles $p_ip_jp_k$ and $p_ip_jp_1$, connecting points $p_i$, $p_j$ and $p_k$ and points $p_i$, $p_j$ and $p_1$, respectively. We can obtain a new triangulation by removing edge $\overline{p_jp_j}$ and inserting edge $\overline{p_kp_1}$ instead. We call such and operation an edge flip. An edge is illegal if we can locally increase the smallest angle by flipping that edge. A Delaunay Triangulation is an angle optimal triangulation— its minimal angle is maximal, i.e., it does not contain any illegal edge.

We start with a big triangle which encompasses all of the location data points which we eliminate at the end of the triangulation process. Given a Delaunay triangulation, $S_n$, of a set of n points $p_n = \{p_1, \ldots, p_n\}$, we can obtain a Delaunay triangulation, $S_{n+1}$, of a set of n+1 points $P_{n+1} = P_n \cup \{p_{n+1}\}$ by splitting the triangle containing $p_{n+1}$ (or the two triangles in case $p_{n+1}$ lies on an edge) and flipping illegal edges that result in the split. In performing the Delaunay triangulation, we initially add the points that are the projection of the locations of the acquisition points on the reference plane.

The Delaunay triangulation may be refined by adding virtual points to intersect large edges. The Delaunay triangulation is continued with the virtual points, thereby keeping the triangulation optimal. The values of the virtual nodes are determined by the approximation function described above. We add virtual points that split edges whose size exceeds a certain threshold. The third dimension of all the points is determined by the approximating function described above.

It is worth noting that if refinement of the triangulation is not desired, we need not compute the function. In other words, the function may be a piece-wise linear one, determined, for example, by the triangulation of the location data.

Not all of the acquisition point locations will necessarily reside at the vertices of the triangulation. This may occur, for example, when two acquisition point locations share their x and y coordinates but have different z coordinates. If desired, The resultant triangulation may be adjusted by translating appropriate vertices to coincide with acquisition point locations.

Figure 3:
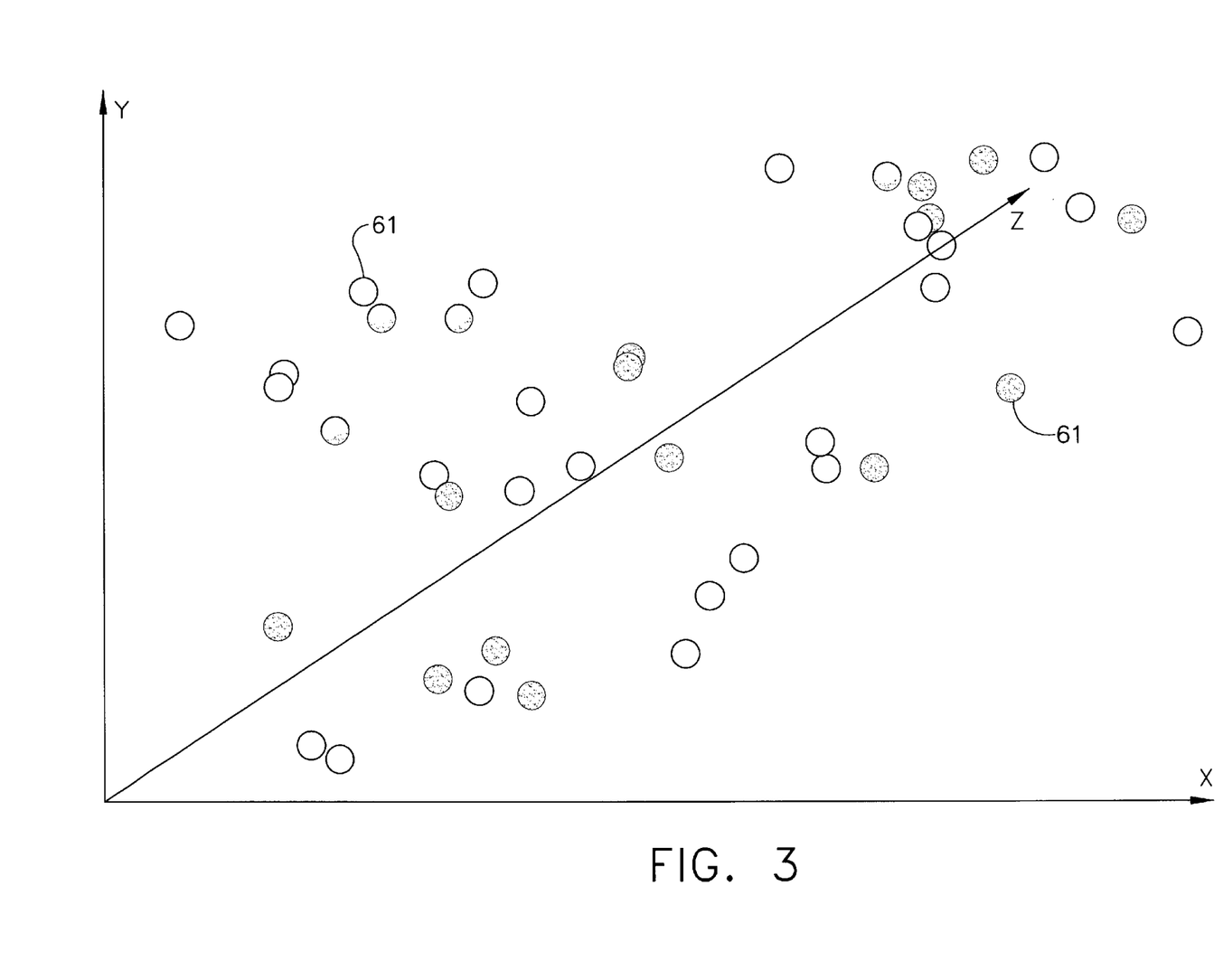
FIG. 3 is a three-dimensional scatter plot of the locations of acquisition points of a portion of an internal surface of a chamber of a heart.
Figure 4:
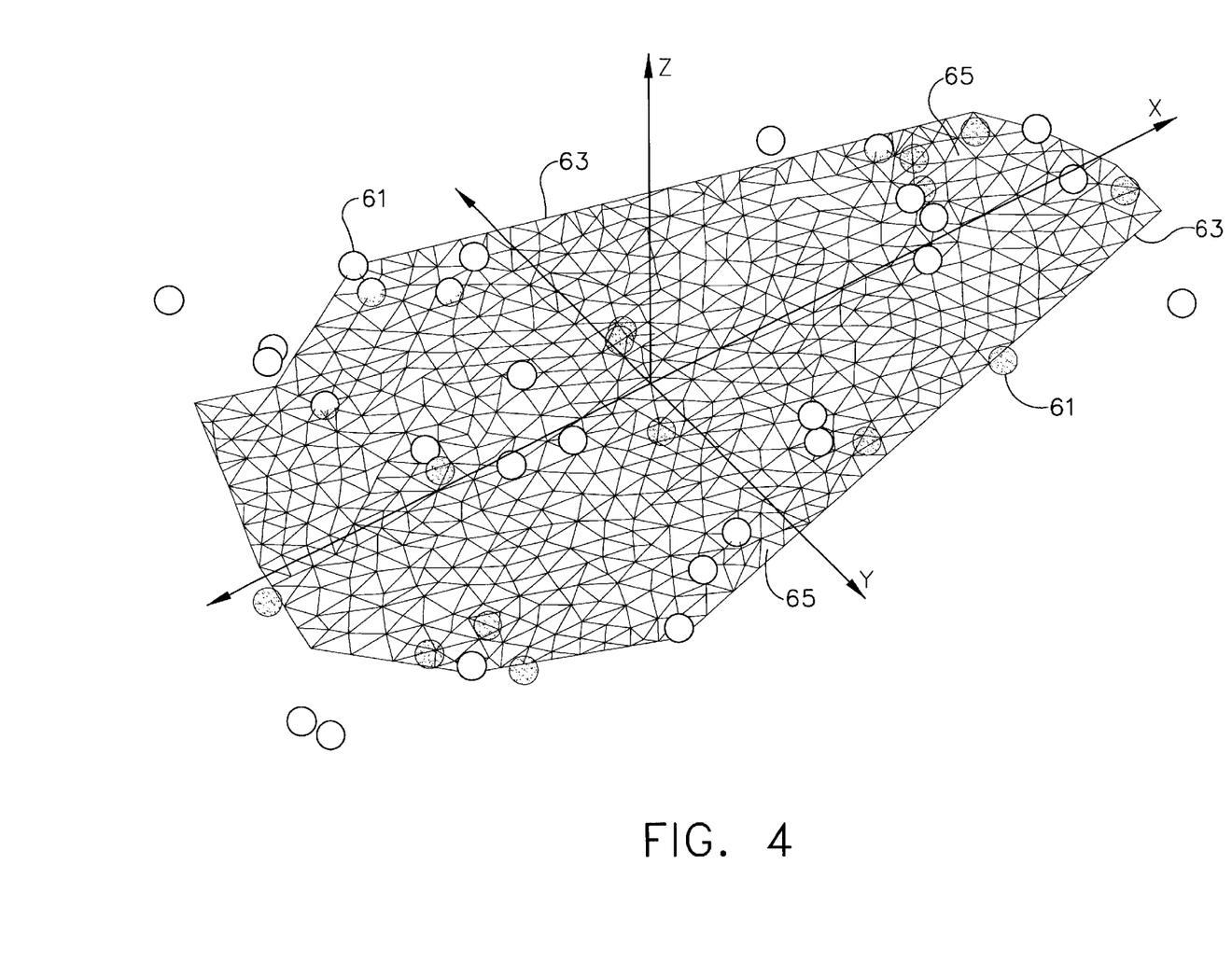
FIG. 4 shows a reference plane computed based on the location of the points of FIG. 3 in which the plane has been tessellated into triangular elements.

FIG. 3 is a three-dimensional scatter plot of the locations of acquisition points 61 of a portion of an internal surface of a chamber of a heart. The acquisition point locations were determined as described above using a catheter of the type shown in FIG. 1 and FIG. 2. FIG. 4 shows the reference plane 63 which approximates the points 61 of FIG. 3. The plane, as shown in FIG. 4, has been tessellated into triangular elements 65. As noted in FIG. 4, the coordinate system has been transformed as a result of the principal component analysis as described above, wherein the X, Y and Z axes are the first, second and third largest eigenvectors, respectively.

Figure 5:
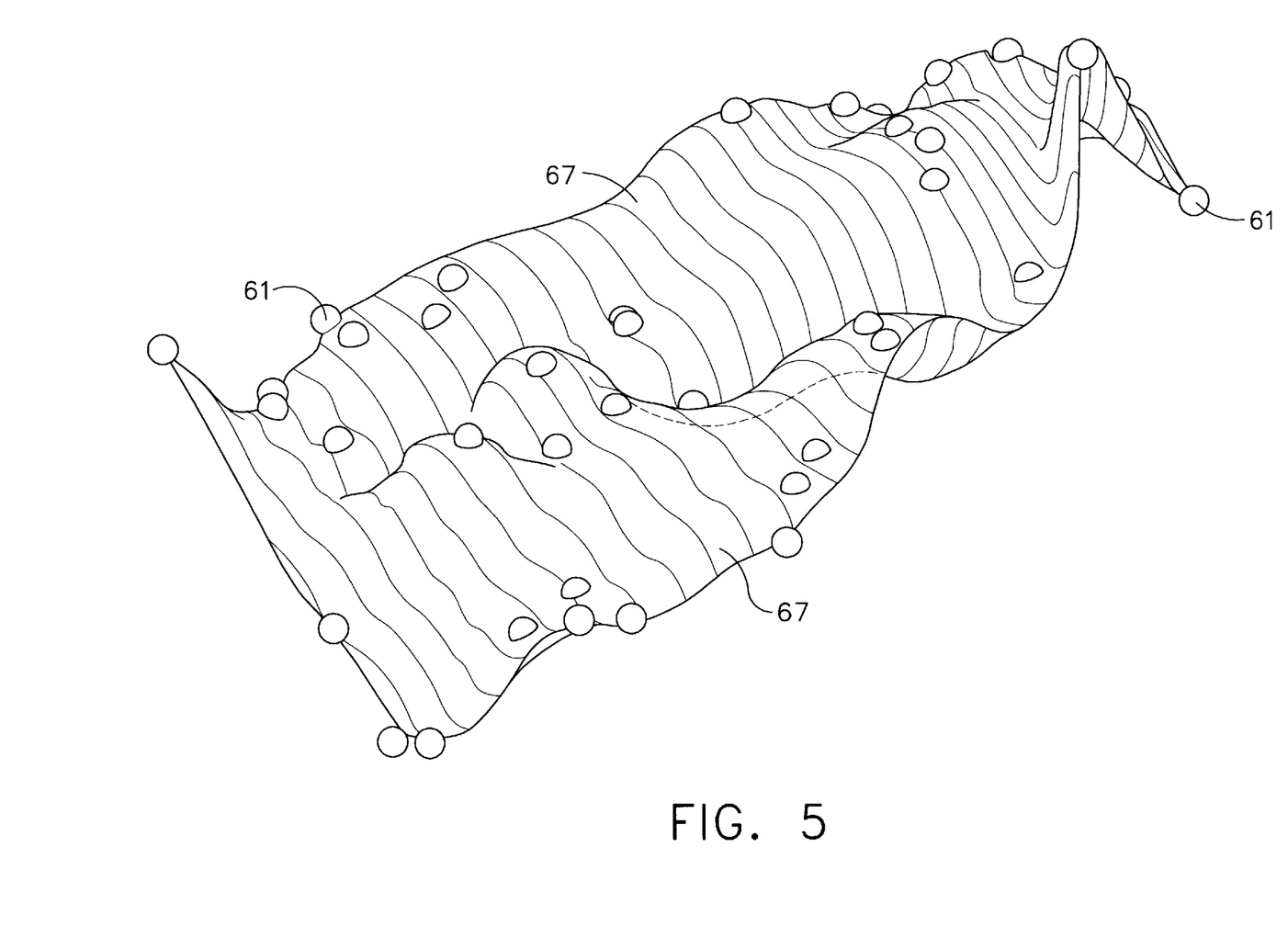
FIG. 5 is a graphical reconstruction of the surface of the portion of the chamber of the heart for which acquisition points are shown in FIG. 3.

FIG. 5 is a graphical reconstruction of the surface 67 of the portion of the chamber of the heart for which acquisition points are shown in FIG. 3. The reconstruction of FIG. 5 shows both the surface 67 as well as the acquisition points 61.

As indicated previously, the collection of location and associated property data permit the calculation of a reconstruction which shows both the geometry of the portion of the organ surface as well as the property of that organ as a function of the geometry. In some embodiments, the property of the tissue at points intermediate the acquisition points may be interpolated based on the values of the property at the acquisition points.

The property may be depicted in the reconstruction in a number of ways. In some embodiments, the value of the property may be printed on the geometrical reconstruction of the portion of the surface of the organ. In other embodiments, the values of the property may be indicated by shading, by numbering or by coloring regions of the reconstruction wherein the shading, numbering or coloring encompass a range of values of the property.

Figure 6:
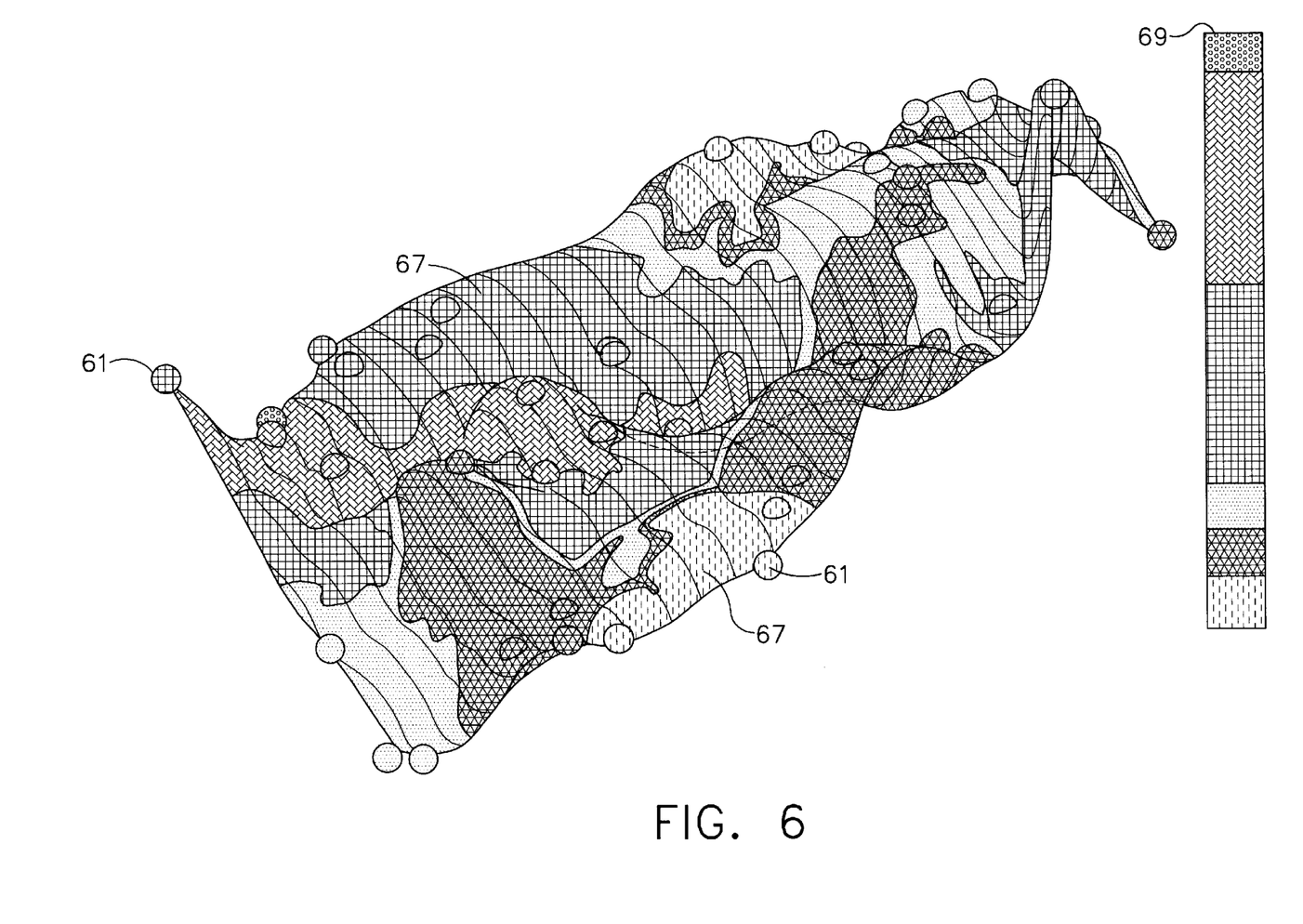
FIG. 6 shows the reconstruction of FIG. 5 wherein the surface is shaded to reflect the local activation time (LAT) of the tissue.

FIG. 6 shows the reconstruction of FIG. 5 wherein the surface is shaded to reflect the local activation time (LAT) of the tissue. Each shading pattern represents a range of activation times. Areas of like shading are activated over the same range of activation times. The reconstruction may be accompanied by a key 69 which provides a visual indicator for the values of the property in the reconstruction. For example, the tissue in the reconstruction of FIG. 6 is broken down into six ranges. The values corresponding to these ranges may be shown next to the key 69.

The reconstruction of a portion of a chamber of a heart, particularly with data indicative of a property of the cardiac tissue, is especially useful in diagnosing and treating pathologies of the cardiac tissue. Where the pathology is an aberrant electrical pathway which may lead to life-threatening arrhythmias, one method of treatment involves local ablation of the cardiac surface. As shown in FIG. 2, ablation may be performed by supplying RF energy to a local site from ablation power source 53 via circuits 40 and cable 25 to electrode 23 contained at distal tip 22 of catheter 21. Alternatively, therapeutics may be delivered to the site of a lesion using a delivery catheter that has position sensing capability as described, for example, in co-pending U.S. patent applications Ser. No 09/19,453 and 09/379,540, the disclosures of which are hereby incorporated herein by reference. U.S. patent application Ser. No. 09/19,453 discloses treatments for ischemia that include growth factors such as fibroblast growth factor and vascular endothelial growth factor as well as genes encoding the growth factor. U.S. patent application Ser. No. 09/379,540 discloses delivering cells such as myoblasts or myocytes to the heart for treatment of ischemia. Alternatively, as disclosed in published PCT application 98/30144, the disclosure of which is incorporated herein by reference, the treatment may involve exposing the heart tissue to laser irradiation to promote revascularization of the heart tissue.

In addition, the method and apparatus of the invention are useful for conducting follow-up studies of the property of cardiac tissue to determine the efficacy of a particular treatment protocol.

What is claimed is:

1. A method of generating a three-dimensional reconstruction of a portion of a surface of an organ, said method comprising the steps of:

a) providing an apparatus having a position sensor for generating signals used to determine location data;

b) acquiring location data at a plurality of acquisition points on said organ surface using said position sensor, wherein each of said acquisition points has a three-dimensional location on said organ surface;

c) computing a two-dimensional reference plane based on said location data;

d) computing a function that describes said surface, wherein each point on said surface is described as a function of said reference plane; and e) bounding said function to a constrained region.

2. The method of claim 1 wherein said plane exhibits errors with respect to said three-dimensional locations of said acquisition points, and wherein said plane is computed by minimizing said errors from said acquisition points to said plane.

3. The method of claim 2 wherein said plane is computed by minimizing the mean square error between said acquisition points and said plane.

4. The method of claim 2 wherein said errors are weighted.

5. The method of claim 4 wherein said errors are weighted by according higher weights to isolated location data points.

6. The method of claim 1 wherein said plane passes through the center of a bounding ellipsoid surrounding said acquisition points.

7. The method of claim 1 wherein said plane passes through the center of mass of a convex hull of the acquisition points.

8. The method of claim 1 wherein said plane passes through the center of mass of the acquisition points.

9. The method of claim 1 wherein the function passes through the location of said acquisition points.

10. The method of claim 1 wherein said function is selected from splines and radial basis functions.

11. The method of claim 1 wherein the value of said function corresponding to each point on said plane is a weighted average of the locations of said acquisition points.

12. The method of claim 11 wherein said locations of said acquisition points are weighted by their respective distances from said point on said plane.

13. The method of claim 1 wherein said function is a piecewise linear function.

14. The method of claim 13 wherein said piecewise linear function is formed by triangulation of said location data points.

15. The method of claim 1 wherein said function is bounded by a convex hull of the projection of said location data points onto said plane.

16. The method of claim 1 which comprises tessellating said function.

17. The method of claim 16 wherein vertices of said tessellation are made to coincide with at least some of said location data points.

18. The method of claim 16 wherein said tessellation is performed by Delaunay triangulation of said reference plane.

19. The method of claim 16 which further comprises refining said tessellation by adding virtual points to said surface.

20. The method of claim 19 wherein the value of said virtual points is determined from said function.

21. The method of claim 1 which further comprises displaying said reconstruction.

22. The method according to claim 1 wherein said location data of each of said points is associated with data characteristic of a property of tissue at said points.

23. The method according to claim 22 which further comprises displaying said reconstruction, wherein said reconstruction further comprises information as to the property of tissue at said data acquisition points.

24. The method according to claim 23 wherein said reconstruction further comprises property information intermediate said acquisition points.

25. The method of claim 23 wherein said reconstruction is colored so as to indicate the value of said property information.

26. The method of claim 1 wherein said organ is a heart.

27. The method of claim 1 wherein said location data is acquired with a catheter comprising a position sensor.

28. The method of claim 27 wherein said position sensor is an electromagnetic position sensor.

29. A method of generating a three-dimensional reconstruction of a portion of a surface of an organ, said method comprising the steps of:

a) providing an apparatus having a position sensor for generating signals used to determine location data;

b) acquiring location data at a plurality of acquisition points on said organ surface using said position sensor, wherein each of said acquisition points has a three-dimensional location on said organ surface;

c) computing a two-dimensional reference plane based on said location data;

d) computing a function that describes said surface, wherein each point on said surface is described as a function of said reference plane; and e) tessellating said functions.

30. The method of claim 29 wherein said tessellation serves to bound said function to a constrained region.

31. The method of claim 30 wherein said tessellation is performed by Delaunay triangulation of said reference plane.

32. The method of claim 31 which further comprises displaying said reconstruction.

33. The method according to claim 31 wherein said location data of each of said points is associated with data characteristic of a property of tissue at said points.

34. The method according to claim 33 which further comprises displaying said reconstruction, wherein said reconstruction further comprises information as to the property of tissue at said data acquisition points.

35. The method according to claim 34 wherein said reconstruction further comprises property information intermediate said acquisition points.

36. The method of claim 34 wherein said reconstruction is colored so as to indicate the value of said property information.

37. The method of claim 31 wherein said organ is a heart.

38. The method of claim 31 wherein said location data is acquired with a catheter comprising a position sensor.

39. The method of claim 38 wherein said position sensor is an electromagnetic position sensor.

* * * * *